(12) United States Patent
Mitra et al.

(10) Patent No.: US 9,815,003 B2
(45) Date of Patent: Nov. 14, 2017

(54) SILICONE DEFOAMER COMPOSITIONS

(71) Applicant: WACKER CHEMICAL CORPORATION, Adrian, MI (US)

(72) Inventors: Amitabha Mitra, Saline, MI (US); Richard Becker, Burghausen (DE); John Richards, Sylvania, OH (US); Margaret Whitton, Jackson, MI (US)

(73) Assignee: WACKER CHEMICAL CORPORATION, Adrian, MI (US)

( * ) Notice: Subject to any disclaimer, the term of this patent is extended or adjusted under 35 U.S.C. 154(b) by 0 days.

(21) Appl. No.: 14/867,499

(22) Filed: Sep. 28, 2015

(65) Prior Publication Data

US 2017/0087483 A1    Mar. 30, 2017

(51) Int. Cl.

| | |
|---|---|
| *C08G 77/08* | (2006.01) |
| *B01D 19/04* | (2006.01) |
| *C07F 7/08* | (2006.01) |
| *C11D 3/00* | (2006.01) |
| *C11D 3/37* | (2006.01) |
| *C08K 3/36* | (2006.01) |
| C08G 77/12 | (2006.01) |
| C08G 77/20 | (2006.01) |
| C08G 77/50 | (2006.01) |
| C08G 77/00 | (2006.01) |

(52) U.S. Cl.
CPC ........ *B01D 19/0409* (2013.01); *C07F 7/0849* (2013.01); *C08K 3/36* (2013.01); *C11D 3/0026* (2013.01); *C11D 3/373* (2013.01); *C08G 77/08* (2013.01); *C08G 77/12* (2013.01); *C08G 77/20* (2013.01); *C08G 77/50* (2013.01); *C08G 77/80* (2013.01)

(58) Field of Classification Search
CPC ........ C08G 77/08; C08G 77/12; C08G 77/20; C08G 77/50
See application file for complete search history.

(56) References Cited

U.S. PATENT DOCUMENTS

| 4,011,247 A * | 3/1977 | Sato ..................... C08G 77/045 |
| | | 528/15 |
| 4,396,524 A | 8/1983 | Hempel et al. |
| 4,639,489 A * | 1/1987 | Aizawa ............. B01D 19/0409 |
| | | 516/123 |
| 6,521,586 B1 * | 2/2003 | Hoogland .......... B01D 19/0404 |
| | | 510/347 |
| 6,521,587 B1 | 2/2003 | L'Hostis et al. |
| 8,084,566 B2 | 12/2011 | Rautschek et al. |
| 8,222,303 B2 | 7/2012 | Herzig et al. |
| 8,461,221 B2 | 6/2013 | Becker et al. |
| 8,536,109 B2 | 9/2013 | Delbrassinne et al. |
| 2011/0294714 A1* | 12/2011 | Delbrassinne ..... B01D 19/0404 |
| | | 510/343 |
| 2014/0289969 A1* | 10/2014 | Sadlowski ............... C11D 1/29 |
| | | 8/137 |
| 2015/0322380 A1* | 11/2015 | Li .......................... C11D 3/124 |
| | | 510/218 |

FOREIGN PATENT DOCUMENTS

| DE | 3805661 A1 | 9/1989 |
| EP | 0 031 532 A1 | 7/1981 |
| EP | 0 217 501 A2 | 4/1987 |
| EP | 0 273 448 A2 | 7/1988 |
| EP | 0 578 424 A2 | 1/1994 |
| EP | 1 075 864 A2 | 2/2001 |
| GB | 639673 | 7/1950 |
| GB | 2 257 709 A | 1/1993 |
| WO | 03/089108 A1 | 10/2003 |
| WO | 2013167430 A1 | 11/2013 |

* cited by examiner

*Primary Examiner* — Margaret Moore
(74) *Attorney, Agent, or Firm* — Brooks Kushman P.C.

(57) ABSTRACT

Defoamer compositions contain a) a two-stage hydrosilylation product of one or more $M_4^H Q$ or $M_3^H T^{phenyl}$ starting materials with a hydrosilylatable composition containing α-methylstyrene, and then with a linear or branched organopolysiloxane bearing at least two hydrosilylatable groups; b) a silicone resin; and c) silica. The defoamers are particularly useful in machine laundering and dishwashing compositions.

21 Claims, 3 Drawing Sheets

SILICONE DEFOAMER COMPOSITIONS

BACKGROUND OF THE INVENTION

1. Field of the Invention

The invention pertains to silicone defoamer compositions containing organopolysiloxane-crosslinked arylalkyl-group-containing T and Q siloxy units.

2. Description of the Related Art

Many aqueous systems foam excessively under agitation, and are thus in need of foam control agents to control the amount of foam generated. The aqueous systems may be of natural or synthetic origin, particularly the latter. Examples include surfactant-laden emulsions from oil and gas recovery, and the so-called "black liquor" from the processing of cellulosic and lignocellulosic fiber-containing materials into paper products. Additional examples include, in particular, aqueous washing compositions for use in laundering and machine dishwashing. While most hand dishwashing compositions are designed to be high foaming to generate a perception of high cleaning activity, the generation of foam in clothes washers and machine dishwashers is known to interfere with cleaning ability. Moreover, excessive foaming can impose a much greater load on the electrical motor driving such devices, to the point of thermal destruction of the motor. The foam additionally presents the possibility of overflow and thus water damage to surrounding areas.

To mitigate these undesirable effects, surfactants used in machine laundering and dishwashing and other fields, have often been of the low foaming type. Unfortunately, cleaning efficiency is frequently compromised by their use. In addition, other ingredients in detergent formulations, for which there are no low foaming substitutes available, may also produce foam.

Thus, in fields where high cleaning efficiency and/or low foam generation is necessary, defoamers have been added to reduce the amount of foam generated and/or to achieve rapid collapse of foam. For this purpose, a wide variety of materials have been proposed over the decades as defoamers. Early on, products such as mineral oils, high boiling petroleum fractions and long-chain alkyl industrial products such as tall oil acids and oxo alcohols have been used. Silicone fluids, particularly polydimethylsiloxanes, have also been used. Most of these materials continue to be used today. However, in many cases, their defoaming activity is too low, or other problems, such as objectionable odor, prevent their use.

Moreover, some defoamers have proven acceptable in some defoaming applications, but not in others. Black liquor, for example, presents a harsh environment which can cause defoamers to decompose and lose their effectiveness, while laundry detergent compositions often contain very high levels of surfactants, and highly alkaline substances, which render many defoamers ineffective.

WO 03/089108 discloses particulate foam control agents containing 1-30 parts by weight of a silicone antifoam, 45-99 parts particulate carrier, 2-50 parts of fluorescent whitening agent, and 1-40 parts binder. The silicone antifoams are conventional linear or branched silicones terminated by trimethylsilyl groups, as disclosed in EP-A-578424. Other silicone antifoams are stated to be disclosed in GB 639673, EP 31532, EP 217501, EP 273,448, DE 38 05 661, GB 2,257,709, and EP-A-1,075,864.

U.S. Pat. No. 6,521,587 B1 attests to the long sought need for defoamers in heavy duty detergent formulations, and proposes use of defoamers containing chain-pendent alkylphenyl-substituted poly(ethyl, methyl)siloxanes; a water-insoluble hydrocarbonoxy oil such as mineral oil, vegetable oil, or insoluble hydrocarbon alcohols, carboxylic acids, or esters; an organosilicon resin, and a hydrophobic filler, the foam control agent being free of polydimethylsiloxanes or containing less than 20 wt. % polydimethylsiloxane based on the weight of the alkylphenyl-substituted organopolysiloxane.

U.S. Pat. No. 8,536,109 B2 discusses the long sought need for efficient defoamers in liquid detergent formulations for laundering, and proposes a mixture of chain-pendent alkaryl-substituted organopolysiloxanes of the same type as in U.S. Pat. No. 6,521,587 B1 together with a silicone "resin" (which non-conventionally also includes linear silicone fluids) as a silicone defoamer, a hydrophobic filler, and a further polyether group-containing silicone resin containing both T and Q units.

WO 2013/167430 A1 discloses the continued need for efficient defoamers, and proposes the use of alkylene-linked organopolysiloxanes, fillers, organopolysiloxane resins, and optionally cyclic organopolysiloxanes, in heavily surfactant-loaded detergent formulations. The preparation of the defoamers starts with the cohydrolysis of vinyl-and hydridofunctional silanes, and generates considerable amounts of byproducts.

U.S. Pat. No. 6,521,586 B1 is similar in disclosure to U.S. Pat. No. 6,521,587 B1, and discloses similar ingredients, but does not require a water-insoluble non-silicon-containing organic fluids.

U.S. Pat. No. 8,084,566 B2 discloses long lasting defoamers which are produced by hydrosilylating an Si—H functional organopolysiloxane with an allyl ether-terminated organopolysiloxane, followed by reaction with a diisocyanate to produce urethane-linked composite polyether/silicone compounds, and which also contain a silicone resin.

U.S. Pat. No. 8,222,303 B2 discloses defoamer compositions containing an organopolysiloxane defoamer, hydrophilic silica, and a polyethersilicone. The defoamers are particularly useful in defoaming black liquor.

U.S. Pat. No. 8,461,221 discloses pulverulent antifoam particles comprising a silicone antifoam absorbed into a porous copolymer of urea, melamine, or a mixture of urea and melamine. The defoamers are said to be particularly useful in laundry detergent formulations.

There has been a continuing long sought need to provide defoamer compositions where one or more of the principal defoamers are easily synthesized, which provide high defoaming activity, and whose structure can be tailored for the particular end use desired.

SUMMARY OF INVENTION

It has now been surprisingly and unexpectedly discovered that efficient and tailorable defoamer compositions can be prepared from a silicone resin component, a silica component, and a silicone defoamer which contains arylalkyl-substituted MQ units and/or arylalkyl-substituted $MT^{phenyl}$ units linked by Si—C bonds to a linear or branched organopolysiloxane.

DETAILED DESCRIPTION OF THE PREFERRED EMBODIMENTS

The silicone defoamer is a two-stage hydrosilylation product of an $M_1^H Q$ organopolysiloxane or of an $M_3^H T^{phenyl}$ organopolysiloxane with a hydrosilylatable hydrocarbon comprising α-methylstyrene in a first stage, and with a di-or polyalkenyl-functional organopolysiloxane in a second stage.

The $M_4^H Q$ organopolysiloxanes have the structure $[M^H\text{-}O]_4 Si$ where Q is $SiO_{4/2}$ and $M^H$ is a monovalent organo-silicon group of the formula $H\text{—}Si(R_2^1)\text{—}$ where $R^1$ is an organo group, preferably a $C_{1\text{-}18}$ alkyl or $C_6$ or $C_{10}$ aryl group, the aryl groups optionally substituted by one or more $C_{1\text{-}18}$ alkyl groups, preferably methyl groups. $R^1$ is preferably $C_{1\text{-}18}$ alkyl, more preferably methyl. $M^H$ groups with one methyl and one long chain alkyl group are also preferred. The most preferred $M_4^H Q$ compound is tetrakis (dimethylsiloxy)silane, "TDSS."

The $M_3^H T^{phenyl}$ starting materials have $M^H$ groups as described above, attached to a phenyl-substituted $SiO_{3/2}$ group, thus having the structure $[M^H\text{-}O]_3\text{—}Si\text{-}\Phi$ where $\Phi$ is a phenyl group. Mixtures of $M_4^H Q$ and $M^H T^{phenyl}$ starting materials may be used.

In the first stage of the reaction, the $M_4^H Q$ or $M_3^H T^{phenyl}$, starting materials are reacted with a hydrosilylatable hydrocarbon comprising α-methylstyrene in the presence of a hydrosilylation catalyst. The $M^H$ groups hydrosilylate the α-methylstyrene and optional further hydrosilylatable higher alkene to substitute the M siloxy group silicon atoms with an Si—C bonded 1-(2-methyl-2-phenyl)ethyl group, which may also be termed an "α-methylphenylethyl" group. It is preferable that at least two $M^H$ groups in the $M_4^H Q$ and/or at least one $M^H$ groups in the $M_3^H T^{phenyl}$ starting materials silylate α-methylstyrene.

Hydrosilylation catalysts and hydrosilylation reaction conditions are well known. The reaction typically takes place to the exclusion of water, under an inert gas atmosphere, such as a dry nitrogen atmosphere. However, any suitable hydrosilylation conditions, as are well known in the art, may be used. The reaction may take place neat, or in the presence of one or more organic solvents, such as toluene, xylene, other aromatic hydrocarbons, paraffinic hydrocarbons, ketones, ester solvents such as ethyl acetate, etc. Neat reaction is preferred. If a higher alkene, e.g. a $C_6$-$C_{20}$ alkene, preferably an α-alkene is present, it is present in a minor portion, <50 mol %, preferably <20 mol % of total hydrosilylatable compounds. Preferably, no higher alkene is present.

Suitable hydrosilylation catalysts include platinum, rhodium, palladium, ruthenium, and iridium, preferably platinum and rhodium. The metals may optionally be fixed to finely divided support materials, such as activated carbon, metal oxides, such as aluminum oxide or silicon dioxide. Preference is given to using platinum and platinum compounds. Particular preference is given to those platinum compounds which are soluble in polyorganosiloxanes. Soluble platinum compounds that can be used include, for example, the platinum-olefin complexes of the formulae $(PtCl_2.olefin)_2$ and $H(PtCl_3.olefin)$, preference being given in this context to the use of alkenes having 2 to 8 carbon atoms, such as ethylene, propylene, isomers of butene and of octene, or cycloalkanes having 5 to 7 carbon atoms, such as cyclopentene, cyclohexene, and cycloheptene. Other soluble platinum catalysts are the platinum-cyclopropane complex of the formula $(PtCl_2.C_3H_6)_2$, the reaction products of hexachloroplatinic acid with alcohols, ethers, and aldehydes or mixtures thereof, or the reaction product of hexachloroplatinic acid with methylvinylcyclotetrasiloxane in the presence of sodium bicarbonate in ethanolic solution. Platinum catalysts with phosphorus, sulfur, and amine ligands can be used as well, e.g., $(Ph_3P)_2PtCl_2$. Particularly preferred are complexes of platinum with vinylsiloxanes, such as sym-divinyltetramethyldisiloxane, and solutions of chloroplatinic acid.

The amount of hydrosilylation catalyst (E) used is governed by the desired reaction rate and also by economic considerations. Typically, per 100 parts by weight of organopolysiloxanes, $1\times10^{-5}$ to $5\times10^{-2}$ parts by weight, preferably $1\times10^{-4}$ to $1\times10^{-2}$, and more particularly $5\times10^{-4}$ to $5\times10^{-3}$ parts by weight of platinum catalysts, calculated as platinum metal, are used. The platinum catalyst may be added in portions during the reaction, especially at the beginning of the second stage.

The mole ratio of α-methylstyrene (and optional higher alkene) to $M_4^H Q$ siloxane is generally at least 1.8:1, more preferably at least 2:1, and preferably not more than 3.2:1, more preferably not more than 3:1. If a ratio of >3:1 is used, the product mixture will contain some $M_4Q$ units where all four M groups are substituted by α-methylphenylethyl groups, and these compounds thus will be unreactive in the second stage hydrosilylation. The mole ratio of α-methylstyrene (and optional higher alkene) to $M_3^H T^{Phenyl}$ siloxane is generally at least 0.8:1, more preferably at least 1:1, and preferably not more than 2.2:1, more preferably not more than 2:1. If a ratio of >2:1 is used, the product mixture will contain some $M_3 T^{Phenyl}$ units where all three M groups are substituted by α-methylphenylethyl groups, and these compounds thus will be unreactive in the second stage hydrosilylation. The presence of such molecules can be tolerated, but their presence is not preferred.

At mole ratios of less than 2:1 in case of $W_4^H Q$, and less than 1:1 in case of $M_3^H T^{Phenyl}$, there may be insufficient α-methylphenylethyl groups to produce sufficient defoamer effectiveness. Moreover, the higher number of residual, unreacted silicon-bonded hydrogen groups may increase any or all of the viscosity, the molecular weight, and the degree of crosslinking of the final product. For example, if the average number of residual Si—H groups is 1, and the hydrosilylatable organopolysiloxane to be used in the second stage has a functionality of 2, an A-B-A structure of relatively low molecular weight will be formed. If, under the same circumstances, the average number of residual Si—H groups is 1 and the functionality of the hydrosilylatable organopolysiloxane is 3, again, a relatively low molecular weight branched polymer of A-B(A)-A structure will be formed.

If, however, both the first stage product and the hydrosilylatable organopolysiloxane have functionalities of close to 2, a linear but higher molecular weight $A\text{-}(B\text{-}A)_n\text{-}A$ structure will be formed. If the chain length n is too large, the product may no longer be fluid. If the functionalities average significantly higher than 2, crosslinked solid elastomers, which are not within the scope of the invention, may be formed. Thus, the number of α-methylphenylethyl groups on average is preferably between 2 and 3 in case of $M_4^H Q$, and between 1 and 2 in case of $M_3^H T^{phenyl}$, and thus the preferred residual Si—H functionality is between 1 and 2.

In the second stage of the reaction, the first stage reaction product is used to hydrosilylate a hydrosilylatable organopolysiloxane. Again, the hydrosilylation catalysts and reaction conditions are conventional.

The hydrosilylatable organopolysiloxane is a linear or branched organopolysiloxane bearing aliphatically unsaturated groups amendable to hydrosilylation. Such groups are well known, and include, for example, alkenyl groups, preferably ω-alkenyl groups. Non-limiting examples include vinyl, allyl, 2-propenyl, isopropenyl, 5-hexenyl, norbornadenyl, cyclohexenyl, ethynyl, and 3-butynyl. Vinyl groups are the preferred hydrosilylatable groups.

The hydrosilylatable groups may be terminal groups or chain-pendent groups, or both. At least two hydrosilylatable groups are present on average, and preferably no more, on average, than 10 such groups are present, more preferably no more than 7.

The organo groups of the hydrosilylatable organopolysiloxane (other than the hydrosilylatable groups) are all those organo groups useful in conventional organopolysiloxanes which are not hydrosilylatable. Examples of such groups are alkyl groups such as $C_{1-18}$ alkyl groups, preferably $C_{1-4}$ alkyl groups, and preferably the methyl group; aryl groups such as phenyl and naphthyl and substituted aryl groups such as $C_{1-18}$ alkyl-substituted phenyl groups and chlorophenyl groups; and aralkyl groups such as phenylethyl and α-methylphenylethyl. Methyl groups and phenyl groups are preferred, and mixtures of methyl and phenyl groups are also preferred.

The preferred hydrosilylatable organopolysiloxanes are thus α,ω-divinylpolydimethylsiloxanes, α,ω-divinylpolydimethylsiloxanes also bearing further, chain-pendent hydrosilylatable groups; and poly(dimethyl)(methylvinyl) siloxanes, where all hydrosilylatable groups are chain-pendent. More than one type and/or functionality of hydrosilylatable organopolysiloxane can be used. Mono-functional hydrosilylatable organopolysiloxanes may also be present in addition to those having functionalities of two or higher, but this is not preferred. If present, these should contain less than 40 mol percent of all hydrosilylatable groups, and in order of increasing preference, less than 30 mol %, less than 20 mol %, less than 15 mol %, less than 10 mol %, and less than 5 mol %.

In general, the hydrosilylation reaction must occur in two steps, as indicated. The two separate hydrosilylations are important in assuring that a majority of α-methylphenylethyl groups are bonded to residues of the $M_4^H Q$ and/or $M_3^H T^{phenyl}$ groups, as opposed to being randomly distributed. Moreover, the combined presence of hydrosilylatable compounds comprising α-methylstyrene and hydrosilylatable organopolysiloxane containing at least two hydrosilylatable groups raises the possibility that extensive crosslinking of the $M_4^H Q$ and/or $M_3^H T^{phenyl}$ groups with the hydrosilylatable organopolysiloxane can occur. Such products are likely to be highly crosslinked solids. In either case, the product will not be that claimed. However, it would not depart from the spirit of the invention to include not more than 30 mol percent, preferably not more than 20 mol percent and most preferably not more than 10 mol percent of total hydrosilylatable organopolysiloxane in the first step, particularly when α-methylstyrene alone or in substantial mol percent is to be used as the hydrosilylatable composition, and so long as a liquid product is obtained. Similarly, similar proportions of <30 mol %, <20 mol %, and <10 mol percent of α-methylstyrene and/or long chain alkene relative to the total amount of α-methylstyrene and long chain alkene may be used in the second step. The goal is to produce products with chain-terminal and/or chain-pendent MQ and $MT^{phenyl}$ groups, the M groups of which preferably contain at least two α-methylphenylethyl groups on average, preferably three α-methylphenylethyl groups in the case of the MQ groups, and preferably two α-methylphenylethyl groups in the case of MT groups.

Following the second stage hydrosilylation, the reaction mixture is preferably devolatized under vacuum, and optionally stripped with the aid of a stripping gas such as dry nitrogen, to remove volatiles and unreacted low molecular weight starting materials or byproducts.

Figure 1:
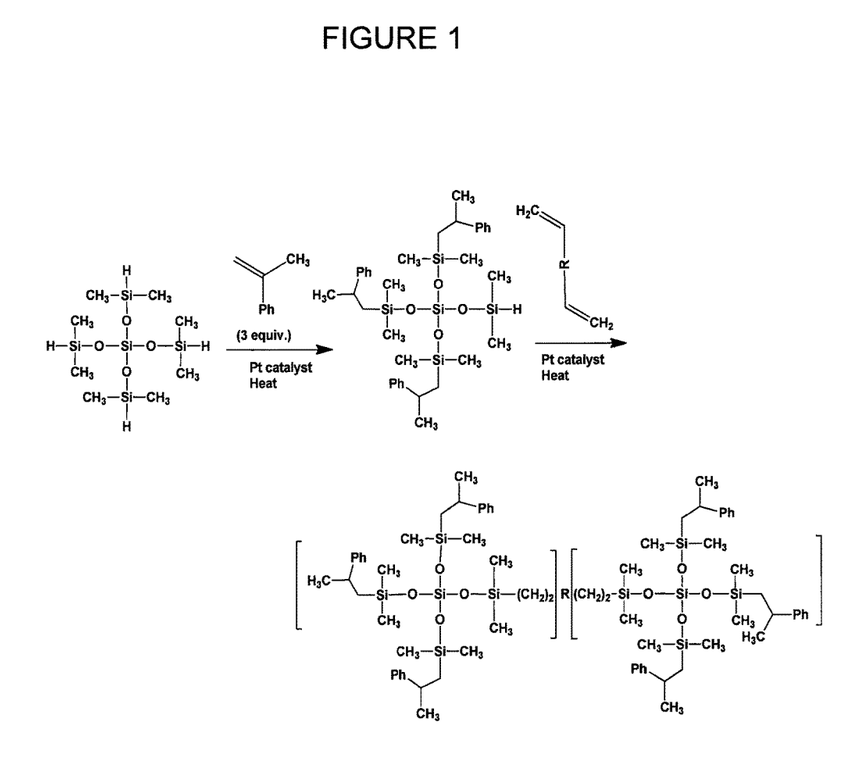
FIG. 1 discloses in schematic form, one embodiment of a synthetic pathway to produce an inventive silicone defoamer component.
Figure 2:
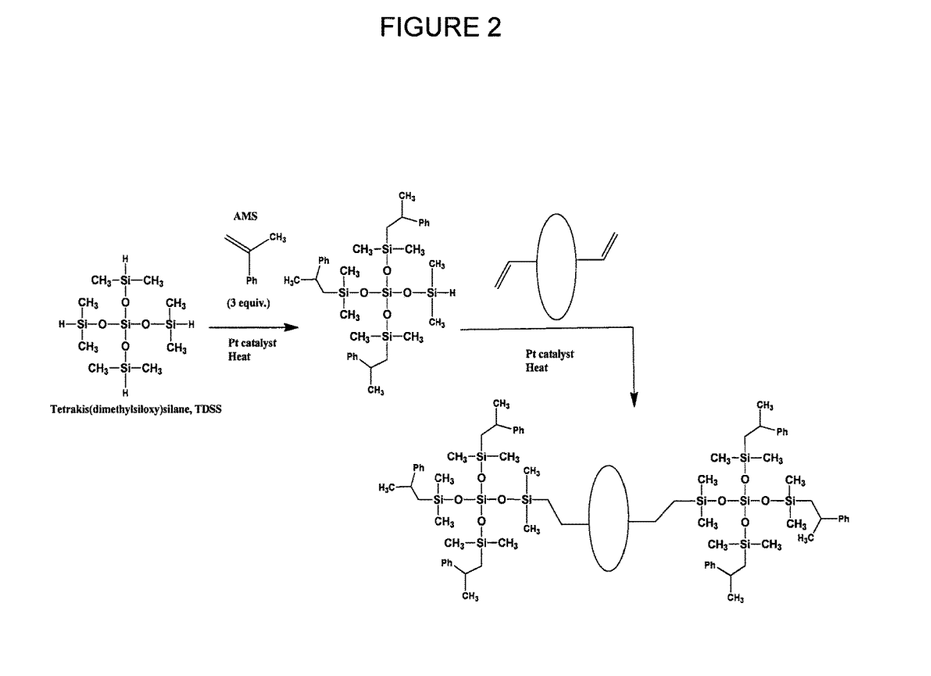
FIG. 2 discloses in schematic form, a second embodiment of a synthetic pathway to produce an inventive silicone defoamer component.
Figure 3:
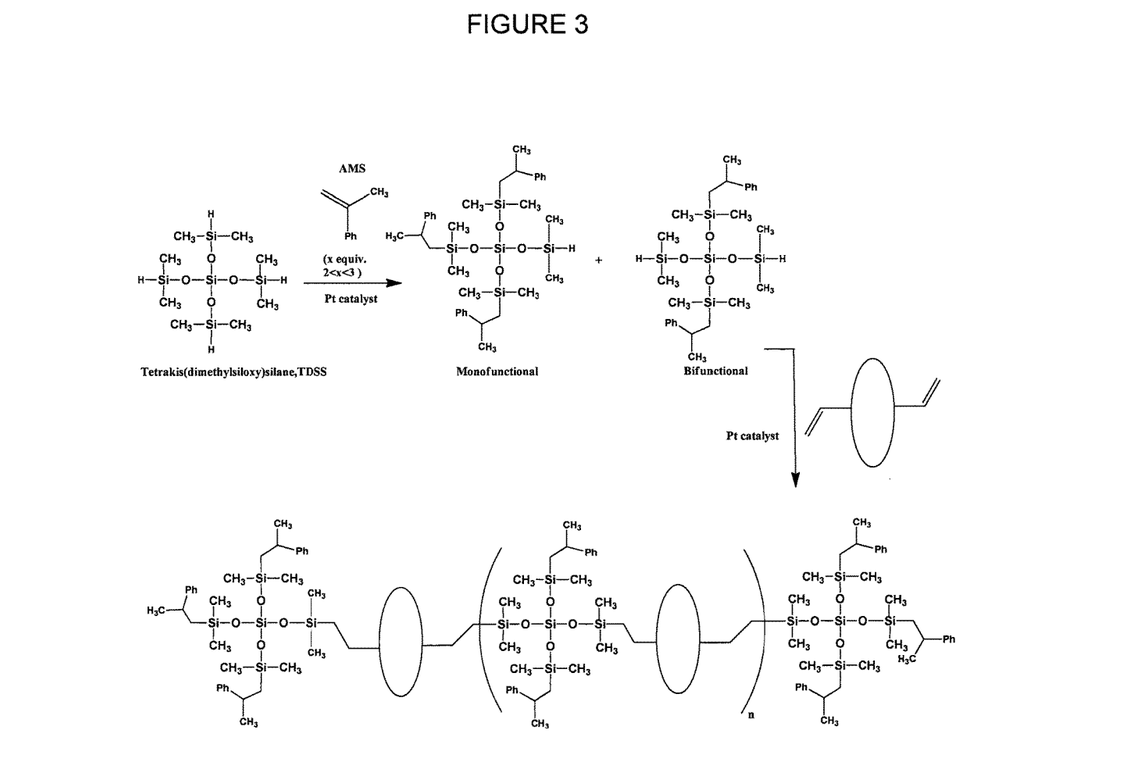
FIG. 3 discloses in schematic form, a third embodiment of a synthetic pathway to produce an inventive silicone defoamer component

Examples of preparation of suitable silicone defoamer molecules are presented in FIGS. 1-3.

In FIG. 1, the $M_4^H Q$ organopolysiloxane has been reacted with three equivalents of α-methylstyrene, and then used to hydrosilylate an α,ω-divinyl polydimethylsiloxane. The result is a simple A-B-A structure.

In FIG. 2, again, 3 equivalents of α-methylstyrene are used, but the hydrosilylatable organopolysiloxane used has a functionality >2, and thus a branched structure is obtained.

In FIG. 3, less than 3 equivalents of α-methylstyrene, in conjunction with a hydrosilylatable organopolysiloxane with a functionality of greater than two, results in a three dimensional multibranched and possibly crosslinked, although still liquid, product. The three dimensional nature of the products of FIGS. 2 and 3 cannot be realistically conveyed in two dimensions, and the "elipse" represents the residue of the hydrosilylatable organopolysiloxane to which further $M^H Q$ or $M^H T^{phenyl}$ groups are bonded by hydrosilylation.

The defoamer compositions of the present invention also contain a silicone resin. The silicone resin may be an MQ resin, an MT resin, an MQT resin, or a T resin. The resin may also include D groups in amounts of less than 20 mol percent of all siloxy groups. As is well known, silicone resins are highly crosslinked, three dimensional, network-like polymers. The silicone resins are solid at room temperature. The meanings of M, D, T, and Q units are well known in silicone resin chemistry, and refer to, in the case of M, D, and T units, organo-substituted siloxy groups with 1, 2, and 3 siloxy bonds, respectively, and thus, 3, 2, and 1 organo groups, respectively. The Q group is the tetravalent $SiO_{4/2}$ group. Preferred resins are MQ resins. These resins are commercially available from numerous sources. A preferred MQ resin is MQ 803, a product of Wacker Chemie, having a content of about 40 mol % $(CH_3)_3SiO_{1/2}$ (M) units, 50 mol % $SiO_{4/2}$ (Q) units, 8 mol % $C_2H_5OSiO_{3/2}$ (T) units, and about 2 mol % uncondensed $HOSiO_{3/2}$ (T) units, with a weight average molecular weight of about 7900 g/mol, relative to polystyrene standard. Preferably, the silicone resins contain no Si—C or Si—O—C bonded polyoxyalkylene groups.

The organo groups of the silicone resins may vary, but are generally lower $C_{1-4}$ alkyl or phenyl, preferably methyl. Some long chain $C_{5-18}$ alkyl groups may also be present. Lower $C_{1-4}$ alkoxy groups are usually present in a minor amount, and Si—OH groups (silanol functionality) are usually present in minor amount as well. The molecular weight $M_w$ may range from 500 to 100,000 Da, more preferably 1000 to 40,000 Da, and most preferably 2000 to 20,000 Da. More than one type of silicone resin may be used.

A third constituent of the inventive defoamer compositions is silica. The silica may be colloidal silica or fumed (pyrogenic) silica, preferably fumed silica, and may have a BET surface area of, for example, 30 m²/g to 400 m²/g, preferably 50 m²/g to 400 m²/g, and more preferably 100 m²/g to 350 m²/g. The silica may be at least partly hydrophobicized, or may be untreated. Untreated hydrophilic silica is preferred. Such silicas, both partially surface modified (partially hydrophobicized) and untreated (hydrophilic), are commercially available from numerous sources in a wide variety of BET surface areas. A particularly preferred silica is HDK® T30, a hydrophilic fumed silica with a BET surface area of about 300 m$^2$/g, available from Wacker Chemie AG, Munich, Germany.

The defoaming compositions of the subject invention may optionally contain other ingredients as well. Especially preferred additional ingredients include other defoamers, such as paraffinic oils, low molecular weight polyolefin wax dispersions, long chain alcohols and their esters; fatty acids; silicone fluids, including both trimethylsilyl-terminated fluids and dimethylsilanol-terminated fluids; and further silicone resins, particularly low molecular weight liquid silicone resins. This list is illustrative, and not limiting.

The defoaming compositions may be prepared by simple but intimate mixing or blending of components. Mixing may take place using conventional stirrers and agitators, for example paddle stirrers, vane stirrers, rotor/stator mixers, impingement mixers, dissolvers, and the like. Preferably, the solid silicone resin is supplied to the mixing apparatus dissolved in a suitable solvent, which may remain in the product or which may subsequently be removed. Suitable solvents include: aromatic solvents and aromatic solvent blends, containing, e.g. toluenes and xylenes, paraffinic hydrocarbons, ketones, ester solvents such as ethyl acetate and t-butylacetate, long chain alkanols, and organopolysiloxane fluids such as trimethylsilyl-terminated polydimethyl siloxanes. Preferred solvents are those which may also exert some defoaming activity, such as higher molecular weight aliphatic hydrocarbons, for example, fractions having boiling points in the range of 70° C. to 350° C., more preferably 100° C. to 300° C., and most preferably 200° C. to 300° C.

The inventive defoaming compositions are preferably used in liquid or solid laundry and machine dishwashing detergent formulations, and the invention thus further pertains to such formulations which include the inventive defoamers. Such formulations contain at least one surfactant, which may be, for example, anionic, cationic, amphoteric, zwitterionic, or non-ionic. The formulations may also include builders, sequestrants, anti-redeposition agents, alkalizing agents, bulking agents, fillers, fragrances, and the like. Such formulations are well known to those skilled in the art.

EXAMPLES

Synthesis of Silicone Fluids
General Synthetic Procedure:

A four-necked round-bottomed flask, equipped with various neck adapters and stopcock-equipped bypass adapter, to accommodate a mechanical stirrer, thermocouple, addition funnel, water condenser, nitrogen gas inlet and outlet, and rubber septum, was used for the hydrosilation. A heating mantle was used for heating the flask. An electronic thermostat was used in conjunction with the thermocouple to control heating of the flask and contents. The preparation was conducted under a mild flow of dry nitrogen gas. Upon completion of reaction, the water condenser was by-passed or removed, and any volatiles were removed under vacuum. The product was cooled to below 40° C. and filtered under air or nitrogen pressure using a 0.45-10 µm nylon or polyester membrane filter with or without a pre-filter. The reactions are highly exothermic and must be controlled by adjusting the temperature and/or reagent addition rate.

Synthesis of Fluid I:

The reaction flask was charged with tetrakis(dimethylsiloxy)silane, TDSS, [130.0 g, 1.20% w/w H content]. The flask was heated to 80° C., alpha-methylstyrene (AMS, 136.1 g) was charged to the addition funnel, and approximately one-sixth of the AMS was added to the flask. The temperature of the flask contents was raised to approximately 100° C., and a solution of chloroplatinic acid in cyclohexanol (1.02% Pt w/w in the alcohol, 93 µL) was added quickly to the stirring (200-255 rpm) mixture in the flask via a syringe. A rapid exotherm ensued. AMS addition from the funnel was continued to keep the temperature in the range of 140-160° C. from the heat of reaction. Upon completion of AMS addition, the mixture was heated at 145° C. for 60 minutes. Vinyl silicone of approximate formula $M^{Vi}D_xM^{Vi}$ (390.7 g, 2.66% w/w vinyl content) was added slowly from the addition funnel. Immediately after the start of the silicone addition, a further aliquot of Pt catalyst solution (93 µL) was added. After the vinyl silicone addition was complete, the mixture was heated for 60 minutes at 155° C. with increased mixing speed (approximately 425 rpm). The reaction mixture was then stripped under vacuum (5-15 mm Hg) at about 155° C. for 30 minutes to remove any residual volatiles. The product was then filtered after cooling to yield an almost colorless transparent liquid. $^1$H NMR analysis showed the expected product. Viscosity: 154 mPa·s.

Synthesis of Fluid II:

The reaction flask was charged with tetrakis(dimethylsiloxy)silane, TDSS [8.0 g, 1.20% w/w H content]. The flask was heated to 80° C., alpha-methylstyrene (AMS, 7.0 g) was charged to the addition funnel, and approximately one-sixth of the AMS was added to the flask. The temperature of the flask contents was raised to approximately 100° C., and a solution of chloroplatinic acid in cyclohexanol (1.02% Pt w/w in the alcohol, 6 µL) was added quickly to the stirring (200-255 rpm) mixture in the flask via a syringe. A rapid exotherm ensued. AMS addition from the funnel was continued to keep the temperature in the range of 140-160° C. from the heat of reaction. Upon completion of AMS addition, the mixture was heated at 145° C. for 30 minutes.

Vinyl silicone of approximate formula $M^{Vi}D_xM^{Vi}$ (310.9 g, 0.309% w/w vinyl content) was added slowly from the addition funnel. Immediately after the start of the silicone addition, a further aliquot of Pt catalyst solution (6 µL) was added. After the vinyl silicone addition was complete, another aliquot of the Pt catalyst solution (6 µL) was added, and the mixture was heated for 60 minutes at 145° C. with increased mixing speed (approximately 450 rpm). The reaction mixture was then stripped under vacuum (5-15 mm Hg) at approximately 155° C. for 30 minutes to remove any residual volatiles. The thick liquid was then filtered after cooling to yield an almost colorless transparent thick liquid. $^1$H NMR analysis showed the expected product. Viscosity: 93,844 mPa·s.

Synthesis of Fluid III:

The reaction flask was charged with tetrakis(dimethylsiloxy)silane, TDSS, [75.0 g, 1.20% w/w H content]. The flask was heated to 80° C., alpha-methylstyrene (AMS, 78.5 g) was charged to the addition funnel, and approximately one-sixth of the AMS was added to the flask. The temperature of the flask contents was raised to about 100° C., and a solution of chloroplatinic acid in cyclohexanol (1% Pt w/w in the alcohol, 54 µL) was added quickly to the stirring (200-255 rpm) mixture in the flask via a syringe. A rapid exotherm ensued. AMS addition from the funnel was continued to keep the temperature in the range of 140-165° C. from the heat of reaction. Another 81 µL of catalyst was added. Upon completion of AMS addition, the mixture was heated at 145° C. for 45 minutes. Silicone resin of approximate formula $M_aD_bT_cT^{Ph}_dD^{Vi}_e$ ($M_{0.19}D_{0.13}T_{0.14}T^{PH}_{0.36}D^{Vi}0.18$), where the M, D, and T units are methyl-substituted (122.5 g, 4.901% w/w vinyl content) was added slowly from the addition funnel. Immediately after the start of the resin addition, an aliquot of Pt catalyst (54 μL) was added. After the resin addition was complete, another aliquot of Pt catalyst (54 μL) was added, and the mixture was heated for 60 minutes at 145° C. The reaction mixture was then stripped under vacuum (5-15 mm Hg) at about 155° C. for 30 minutes to remove any residual volatiles. The brownish product was then filtered after cooling to yield a dark amber colored transparent liquid. $^1$H NMR analysis showed the expected product. Viscosity: 1569 mPa·s.

Synthesis of Fluid IV:

The reaction flask was charged with tetrakis(dimethylsiloxy)silane, TDSS, [75.0 g, 1.20% w/w H content]. The flask was heated to 80° C., alpha-methylstyrene (AMS, 73.3 g) was charged to the addition funnel, and approximately one-sixth of the AMS was added to the flask. The temperature of the flask contents was raised to approximately 100° C., and a solution of chloroplatinic acid in dipropyleneglycol monobutyl ether (0.52% Pt w/w in the ether, 109 μL) was added quickly to the stirring (200-255 rpm) mixture in the flask via a syringe. A rapid exotherm ensued. AMS addition from the funnel was continued to keep the temperature in the range of 140-165° C. from the heat of reaction. Upon completion of AMS addition, the mixture was heated at 145° C. for 30 minutes. Silicone resin of approximate formula $M_aD_bT_cT^{Ph}_dD^{Vi}_e$ (147.0 g, 4.901% w/w vinyl content) was added slowly from the addition funnel. Immediately after the start of the resin addition, an aliquot of Pt catalyst solution (109 μL) was added. After the resin addition was complete, another aliquot of Pt catalyst solution (54 μL) was added, and the mixture was heated for 60 minutes at 155° C. with increased mixing speed (approximately 300 rpm). The reaction mixture was then stripped under vacuum (5-15 mm Hg) at about 155° C. for 30 minutes to remove any residual volatiles. The dark amber colored product was then filtered after cooling to yield a dark amber colored transparent liquid. $^1$H NMR analysis showed the expected product. Viscosity: 8300 mPa·s.

Synthesis of Fluid V:

The reaction flask was charged with tetrakis(dimethylsiloxy)silane, TDSS, [75.0 g, 1.20% w/w H content]. The flask was heated to 80° C., alpha-methylstyrene (AMS, 72.0 g) was charged to the addition funnel, and approximately one-sixth of the AMS was added to the flask. The temperature of the flask contents was raised to approximately 100° C., and a solution of chloroplatinic acid in dipropyleneglycol monobutyl ether (0.52% Pt w/w in the ether, 109 μL) was added quickly to the stirring (200-255 rpm) mixture in the flask via a syringe. A rapid exotherm ensued. AMS addition from the funnel was continued to keep the temperature in the range of 140-165° C. from the heat of reaction. Upon completion of AMS addition, the mixture was heated at 145° C. for 30 minutes. Silicone resin of approximate formula $M_aD_bT_cT^{Ph}_dD^{Vi}_e$ (153.2 g, 4.901% w/w vinyl content) was added slowly from the addition funnel. Immediately after the start of the resin addition, an aliquot of Pt catalyst solution (109 μL) was added. After the resin addition was complete, the mixture was heated for 60 minutes at 150° C. with increased mixing speed (approximately 425 rpm). The reaction mixture was then stripped under vacuum (5-25 mm Hg) at about 150° C. for 30 minutes to remove any residual volatiles. The dark amber colored product was then filtered after cooling to yield a dark amber colored transparent liquid. $^1$H NMR analysis showed the expected product. Viscosity: 16,111 mPa·s.

Synthesis of Fluid VI:

The reaction flask was charged with tetrakis(dimethylsiloxy)silane, TDSS, [75.0 g, 1.20% w/w H content]. The flask was heated to 80° C., alpha-methylstyrene (AMS, 77.2 g) was charged to the addition funnel, and approximately one-sixth of the AMS was added to the flask. The temperature of the flask contents was raised to approximately 100° C., and a solution of chloroplatinic acid in dipropyleneglycol monobutyl ether (0.52% Pt w/w in the ether, 109 μL) was added quickly to the stirring (200-255 rpm) mixture in the flask via a syringe. A rapid exotherm ensued. AMS addition from the funnel was continued to keep the temperature in the range of 140-160° C. from the heat of reaction. Upon completion of AMS addition, the mixture was heated at 145° C. for 30 minutes. Silicone resin of approximate formula $M_aD_bT_cT^{Ph}_dD^{Vi}_e$ (128.6 g, 4.901% w/w vinyl content) was added slowly from the addition funnel. Immediately after the start of the resin addition, an aliquot of Pt catalyst solution (109 μL) was added. After the resin addition was complete, the mixture was heated for 60 minutes at 150° C. with increased mixing speed (approximately 400 rpm). The reaction mixture was then stripped under vacuum (5-25 mm Hg) at about 155° C. for 30 minutes to remove any residual volatiles. The dark amber colored product was then filtered after cooling to yield a dark amber colored transparent liquid. $^1$H NMR analysis showed the expected product. Viscosity: 2085 mPa·s.

Synthesis of Fluid VII:

The reaction flask was charged with tetrakis(dimethylsiloxy)silane, TDSS, [75.0 g, 1.20% w/w H content]. The flask was heated to 80° C., alpha-methylstyrene (AMS, 75.9 g) was charged to the addition funnel, and approximately one-sixth of the AMS was added to the flask. The temperature of the flask contents was raised to approximately 100° C., and a solution of chloroplatinic acid in dipropyleneglycol monobutyl ether (0.52% Pt w/w in the ether, 109 μL) was added quickly to the stirring (200-255 rpm) mixture in the flask via a syringe. A rapid exotherm ensued. AMS addition from the funnel was continued to keep the temperature in the range of 140-160° C. from the heat of reaction. Upon completion of AMS addition, the mixture was heated at 145° C. for 30 minutes. Silicone resin of approximate formula $M_aD_bT_cT^{Ph}_dD^{Vi}_e$ (134.8 g, 4.901% w/w vinyl content) was added slowly from the addition funnel. Immediately after the start of the resin addition, an aliquot of Pt catalyst solution (109 μL) was added. After the resin addition was complete, the mixture was heated for 60 minutes at 150° C. with increased mixing speed (approximately 400 rpm). The reaction mixture was then stripped under vacuum (5-25 mm Hg) at about 155° C. for 30 minutes to remove any residual volatiles. The dark amber colored product was then filtered after cooling to yield a dark amber colored transparent liquid. $^1$H NMR analysis showed the expected product. Viscosity: 2909 mPa·s.

Synthesis of Fluid VIII:

The reaction flask was charged with tetrakis(dimethylsiloxy)silane, TDSS, [75.0 g, 1.20% w/w H content]. The flask was heated to 80° C., alpha-methylstyrene (AMS, 74.6 g) was charged to the addition funnel, and approximately one-sixth of the AMS was added to the flask. The temperature of the flask contents was raised to approximately 100° C., and a solution of chloroplatinic acid in dipropyleneglycol monobutyl ether (0.52% Pt w/w in the ether, 109 μL) was added quickly to the stirring (200-255 rpm) mixture in the flask via a syringe. A rapid exotherm ensued. AMS addition from the funnel was continued to keep the temperature in the range of 140-160° C. from the heat of reaction. Upon completion of AMS addition, the mixture was heated at 145° C. for 30 minutes. Silicone resin of approximate formula $M_a D_b T_c T^{Ph}_d D^{Vi}_e$ (140.9 g, 4.901% w/w vinyl content) was added slowly from the addition funnel. Immediately after the start of the resin addition, an aliquot of Pt catalyst solution (109 µL) was added. After the resin addition was complete, the mixture was heated for 60 minutes at 150° C. with increased mixing speed (approximately 325 rpm). The reaction mixture was then stripped under vacuum (5-25 mm Hg) at about 155° C. for 30 minutes to remove any residual volatiles. The dark amber colored product was then filtered after cooling to yield a dark amber colored transparent liquid. $^1$H NMR analysis showed the expected product. Viscosity: 3587 mPa·s.

Preparation of Defoamer Compounds:

Materials:

Silicone oil: AK 8000: A polydimethylsiloxane terminated with trimethylsiloxane groups and having a viscosity of 0.008 m$^2$/s.

Fluids I-VIII: synthesized according to the procedures described above.

Defoamer oil: a blend of silicone resin MQ 803 and Exxsol D 100 ULA. Exxsol D 100 ULA is a hydrocarbon mixture having a boiling range of 210-280° C. obtained from ExxonMobil. Silicone resin MQ 803 is solid at room temperature and is composed (by $^{29}$Si NMR and IR analysis) of 40 mol % $(CH_3)_3SiO_{1/2}$, 50 mol % $SiO_{4/2}$, 8 mol % $C_2H_5OSiO_{3/2}$, and 2 mol % $HOSiO_{3/2}$ units, with a weight-average molar mass of 7900 g/mol (with reference to polystyrene standard).

Methanolic Potassium Hydroxide (20% Solution)

Filler: HDK T 30: a hydrophilic fumed silica having a surface area of 300 m$^2$/g, obtainable from Wacker Chemie AG Munich.

Method:

The silicone fluid (silicone oil AK 8000 for comparative example C1 or either of the fluids I-VIII for inventive examples 1-8 below in Table 1), defoamer and the methanolic potassium hydroxide solution were weighed together in a 250 mL beaker and mixed briefly with a spatula. The filler HDK was added and mixed again until all of the HDK blended in to form a homogeneous mixture. The mixture was mixed immediately for 10 minutes with a dissolver at 800 rpm. After that, the mixture was heated in a drying oven at 150° C. for 4 h, cooled down to room temperature and mixed with the dissolver for another 2 min at 800 rpm.

TABLE 1

Composition of defoamer compounds:

| | Component | Example C1 (Comp. Example) | Ex. 1 | Ex. 2 | Ex. 3 | Ex. 4 | Ex. 5 | Ex. 6 | Ex. 7 | Ex. 8 |
|---|---|---|---|---|---|---|---|---|---|---|
| A | Silicone Oil AK 8000 | 87.39 | — | — | — | — | — | — | — | — |
| | Fluid I | — | 87.39 | — | — | — | — | — | — | — |
| | Fluid II | — | — | 87.39 | — | — | — | — | — | — |
| | Fluid III | — | — | — | 87.39 | — | — | — | — | — |
| | Fluid IV | — | — | — | — | 87.39 | — | — | — | — |
| | Fluid V | — | — | — | — | — | 87.39 | — | — | — |
| | Fluid VI | — | — | — | — | — | — | 87.39 | — | — |
| | Fluid VII | — | — | — | — | — | — | — | 87.39 | — |
| | Fluid VIII | — | — | — | — | — | — | — | — | 87.39 |
| B | Defoamer Oil | 5.91 | 5.91 | 5.91 | 5.91 | 5.91 | 5.91 | 5.91 | 5.91 | 5.91 |
| C | Methanolic KOH (20% concentration) | 0.74 | 0.74 | 0.74 | 0.74 | 0.74 | 0.74 | 0.74 | 0.74 | 0.74 |
| D | HDK T 30 | 5.96 | 5.96 | 5.96 | 5.96 | 5.96 | 5.96 | 5.96 | 5.96 | 5.96 |

Viscosities of the Defoamer Compounds:

| | Viscosity (mPa · s) |
|---|---|
| Ex C1 | 37,920 |
| Ex. 1 | 1620 |
| Ex. 2 | 500,000 |
| Ex. 3 | 8720 |
| Ex. 4 | 60,500 |
| Ex. 5 | 155,000 |
| Ex. 6 | 13,200 |
| Ex. 7 | 16,200 |
| Ex. 8 | 19,700 |

Tests of Defoamer Effectiveness:

1. Antifoam Index AFI

In an apparatus in accordance with DE-A 25 51 260, 200 ml of a 4% strength by weight aqueous solution of a sodium alkylsulfonate (Mersolat™) containing 10 mg of the defoamer under investigation (in solution in 10 times the amount of methyl ethyl ketone) are foamed for 1 minute using two counterrotating stirrers. Subsequently, the collapse of the foam is recorded. The area of the plot of foam height versus time is used to calculate the antifoam index (Table 2). The lower this index, the more effective is the defoamer.

TABLE 2

Antifoam index of defoamer compositions:

| Example | Antifoam Index |
|---|---|
| Ex C1 (comparative example) | 234 |
| Ex. 1 | 657 |
| Ex. 2 | 590 |
| Ex. 3 | 165 |
| Ex. 4 | 267 |
| Ex. 5 | 392 |

TABLE 2-continued

Antifoam index of defoamer compositions:

| Example | Antifoam Index |
|---|---|
| Ex. 6 | 110 |
| Ex. 7 | 130 |
| Ex. 8 | 157 |

2. Washing Machine Test Using a Powder Detergent

Antifoam powders were prepared by mixing the antifoam compounds (prepared according to the comparative example C1 and the inventive examples 1-8) according to the following composition:

| Component | Weight % | Amount (g) |
|---|---|---|
| Antifoam compounds (either from examples C1 and 1-8) | 15.0 | 22.50 |
| Pergopak M (polymethyl urea resin with approx. 0.6% reactive methylol groups; obtained from Albemarle Corporation) | 5.0 | 7.50 |
| Sodium sulphate | 40.0 | 60.0 |
| Sodiumhydrogencarbonate | 40.0 | 60.0 |

The resulting mixtures were free flowing powders.

For evaluation of the defoamer powders prepared as above, the powders were added to 130 g of a defoamer-free washing powder (TWM ECE-2 from wfk-Testgewebe Gmbh, Germany) at different weight percentage levels (see Table 3). The washing powder was then introduced together with 3500 g of clean cotton laundry into a drum-type washing machine (Miele Novotronic W918 without Fuzzy Logic). Subsequently, the wash program was started (temperature: 40° C., water hardness: 3° dH), and the foam profile was analyzed with a ContiWashCam foam measurement system over a period of 55 minutes. The system takes a picture of the foam level at the center of the washing machine window every minute. All pictures are compared with a reference picture. The automated program detects the foam level and calculates it into percentage foam height. The wash cycle is divided into three segments and the average foam heights are calculated as average of the three wash cycles and are reported. The lower the average percentage, the more effective is the defoamer over the period as a whole.

The test results for powder defoamer are summarized below in TABLE 3:

TABLE 3

Washing machine test results for powder detergents

| Example | % active dosage of defoamer compound in the detergent | Foam height during wash cycle % |
|---|---|---|
| Ex C1 (comparative example) | 0.13 | 56 |
| Ex. 1 | 0.13 | 71 |
| Ex. 2 | 0.13 | 91 |
| Ex. 3 | 0.13 | 2 |
| Ex. 4 | 0.0325 | 22 |
| Ex. 5 | 0.0325 | 44 |

According to the test results, Examples 3, 4 and 5 showed better defoaming performance in powder detergents (as evidenced by the % foam heights in the wash cycles) in the washing machine compared to the comparative example C1. Examples 4 and 5 showed this improved performance even at much lower dosage level relative to the comparison.

3. Washing Machine Test Using a Liquid Detergent:

Defoamer compounds were added to 60 g of the defoamer-free liquid detergent LD886 at different weight percentage levels (see Table 4). The liquid detergent LD886 has the following composition:

| Component | Weight % |
|---|---|
| Deionized water | 65.1 |
| Isotridecylalcohol | 16.9 |
| Sodiumdoceylbenzenesulphonate | 5.7 |
| Sodiumlaurylsulphate | 5.7 |
| 1.2-propanediol | 5.6 |
| Trisodiumcitrate-2-hydrate | 1.0 |

The liquid detergents containing the defoamers were then introduced together with 3500 g of clean cotton laundry into a drum-type washing machine (Miele Novotronic W918 without Fuzzy Logic). Subsequently the wash program was started (temperature: 40° C., water hardness: 3° dH), and the foam profile was analyzed with a ContiWashCam foam measurement system over a period of 55 minutes. The system takes a picture of the foam level at the center of the washing machine window every minute. All pictures are compared with a reference picture. The automated program detects the foam level and calculates it into percentage foam height. The wash cycle is divided into three segments and the average foam heights are calculated as average of the three wash cycles and are reported. The lower the average percentage, the more effective is the defoamer over the period as a whole.

TABLE 4

Results for liquid detergents

| Example | % active dosage of defoamer compound in the detergent | Foam height during wash cycle % |
|---|---|---|
| Ex. C1 (comparative example) | 0.3 | 13 |
| Ex. 3 | 0.075 | 2 |
| Ex. 6 | 0.075 | 8 |
| Ex. 7 | 0.075 | 24 |
| Ex. 8 | 0.075 | 13 |

According to the test results, examples 3, 6, 7 and 8 showed similar or better defoaming performance in the liquid detergent formulations (as evidenced by the % foam heights in the wash cycles) in the washing machine even at lower dosage level compared to the comparative example C1.

It should be noted that while some inventive defoamer compositions performed worse than the comparative example, performance is highly dependent upon the nature of the liquid being defoamed, e.g. content and type of surfactants and other components, etc., and may be significantly better than the comparative example in other formulations, or in other applications previously mentioned.

While exemplary embodiments are described above, it is not intended that these embodiments describe all possible forms of the invention. Rather, the words used in the specification are words of description rather than limitation, and it is understood that various changes may be made without departing from the spirit and scope of the invention.

Additionally, the features of various implementing embodiments may be combined to form further embodiments of the invention.

What is claimed is:

1. A defoamer composition, comprising:
   a) a liquid organopolysiloxane prepared by
      a)i) in a first step, hydrosilylating an $M_4^H Q$ siloxane, a $M_3^H T^{phenyl}$ siloxane, or a mixture comprising an $M_4^H Q$ and/or $M_3^H T^{phenyl}$ siloxane wherein $M_4^H Q$ siloxane has the structure $[M^H\text{-}O]_4 Si$ and $M_3^H T^{phenyl}$ siloxane has the structure $[M^H\text{-}O]_3 Si\text{-}\Phi$ where $\Phi$ is a phenyl group and $M^H$ is a monovalent organosilicon group of the formula $H\text{—}Si(R^1_2)\text{—}$ where $R^1$ is a $C_{1-18}$ alkyl or $C_6$ or $C_{10}$ aryl group, the aryl groups optionally substituted by one or more $C_{1-18}$ alkyl groups,
      with a hydrosilylatable composition containing at least 60 mol percent, based on total mols of the hydrosilylatable composition, of α-methylstyrene, to produce a first stage reaction product still containing Si—H bonded hydrogen; and
      a)ii) in a second step, hydrosilylating an organopolysiloxane bearing two or more hydrosilylatable groups with the first stage reaction product to produce a liquid organopolysiloxane;
   b) at least one silicone resin; and
   c) particulate silica.

2. The defoamer composition of claim 1, wherein the organopolysiloxane bearing two or more hydrosilylatable groups is a vinyl-functional organopolysiloxane.

3. The defoamer composition of claim 1, wherein the organopolysiloxane bearing two or more hydrosilylatable groups is an α,ω-dialkenyl-organopolysiloxane, an α,ω-dialkenyl-organopolysiloxane also containing at least one further chain-pendent Si—C bonded alkenyl group, an organopolysiloxane bearing only chain-pendent alkenyl groups, or a mixture thereof.

4. The defoamer composition of claim 3, wherein the alkenyl groups are vinyl groups.

5. The defoamer composition of claim 1, wherein the hydrosilylatable composition of the first step consists of α-methylstyrene.

6. The defoamer composition of claim 1, wherein the hydrosilylatable composition of the first step comprises α-methylstyrene and not more than 40 mol percent, based on total mols of hydrosilylatable groups in the hydrosilylatable composition, of a $C_{6-18}$ alkene.

7. The defoamer composition of claim 1, wherein the hydrosilylatable composition of the first step is present in an amount of from 1.8 to 3.2 mols of hydrosilylatable groups per mol of $M_4^H Q$ siloxane and 0.8 to 2.2 mols of hydrosilylatable groups per mol of $M_3^H T^{phenyl}$ siloxane.

8. The defoamer composition of claim 1, wherein the $M_4^H Q$ siloxane comprises tetrakis(dimethylsiloxy)silane.

9. The defoamer composition of claim 1, wherein at least one particulate silica is fumed silica having a BET surface area of from 30 m²/g to 400 m²/g.

10. A process for the preparation of a defoamer composition of claim 1, comprising:
    mixing a liquid organopolysiloxane a) with silicone resin b) and particulate silica c).

11. The process of claim 10, wherein the silicone resin b) is first dissolved in a hydrocarbon(oxy) solvent prior to mixing with silica c).

12. The process of claim 11, wherein the hydrocarbon (oxy) solvent is a paraffinic hydrocarbon or mixture of paraffinic hydrocarbons, boiling in the range of from 70° C. to 350° C.

13. The process of claim 10, further comprising adding a base to the mixture of a), b), and c), and heating the resultant mixture.

14. The process of claim 13, wherein the base comprises aqueous or alcoholic sodium hydroxide or potassium hydroxide, or alcoholic sodium alkoxide or potassium alkoxide.

15. An organopolysiloxane, prepared by the process of:
    i) in a first step, hydrosilylating an $M_4^H Q$ siloxane, a $M_3^H T^{phenyl}$ siloxane, or a mixture comprising an $M_4^H Q$ and/or $M_3^H T^{phenyl}$ siloxane in the presence of a hydrosilylation catalyst, wherein $M_4^H Q$ siloxane has the structure $[M^H\text{-}O]_4 Si$ and $M_3^H T^{phenyl}$ siloxane has the structure $[M^H\text{-}O]_3 Si\text{-}\Phi$ where $\Phi$ is a phenyl group and $M^H$ is a monovalent organosilicon group of the formula $H\text{—}Si(R^1_2)\text{—}$ where $R^1$ is a $C_{1-18}$ alkyl or $C_6$ or $C_{10}$ aryl group, the aryl groups optionally substituted by one or more $C_{1-18}$ alkyl groups, with a hydrosilylatable composition containing at least 60 mol percent, based on total mols of the hydrosilylatable composition, of α-methylstyrene, to produce a first stage reaction product still containing Si—H bonded hydrogen; and
    ii) in a second step, without removing the hydrosilylation catalyst from the first step, hydrosilylating an organopolysiloxane bearing two or more hydrosilylatable groups with the first stage reaction product to produce a liquid organopolysiloxane.

16. The organopolysiloxane of claim 15, wherein the organopolysiloxane bearing two or more hydrosilylatable groups is a vinyl-functional organopolysiloxane.

17. The organopolysiloxane of claim 15, wherein the hydrosilylatable composition of the first step consists of α-methylstyrene.

18. The organopolysiloxane of claim 15, wherein the hydrosilylatable composition of the first step comprises α-methylstyrene and not more than 40 mol percent, based on total mols of hydrosilylatable groups in the hydrosilylatable composition, of a $C_{6-18}$ alkene.

19. The organopolysiloxane of claim 15, wherein the hydrosilylatable composition of the first step is present in an amount of from 1.8 to 3.2 mols of hydrosilylatable groups per mol of $M_4^H Q$ siloxane and 0.8 to 2.2 mols of hydrosilylatable groups per mol of $M_3^H T^{phenyl}$ siloxane.

20. The organopolysiloxane of claim 15, wherein the $M_4^H Q$ siloxane comprises tetrakis(dimethylsiloxy)silane.

21. In a detergent formulation employing a defoamer composition, the improvement comprising including at least one defoamer composition of claim 1 in the detergent formulation.

* * * * *